United States Patent [19]

Takase et al.

[11] 3,932,554

[45] Jan. 13, 1976

[54] ISOMERIZATION OF SATURATED HYDROCARBONS WITH MORDENITE CATALYST CONTAINING FLUORINE AND CHLORINE

[75] Inventors: Sinji Takase, Kawasaki; Tomonori Shioiri, Yokohama; Masaru Ushio, Kawasaki, all of Japan

[73] Assignee: Nippon Oil Company Ltd., Nishi Shimba, Japan

[22] Filed: July 15, 1974

[21] Appl. No.: 488,540

Related U.S. Application Data

[63] Continuation of Ser. No. 207,523, Dec. 23, 1971, abandoned.

[30] Foreign Application Priority Data

Apr. 13, 1971 Japan............................ 46-26120

[52] U.S. Cl............................ 260/683.68; 252/441
[51] Int. Cl.²........................................ C07C 5/30

[58] Field of Search............... 260/683.68, 683.65; 252/455 Z

[56] References Cited
UNITED STATES PATENTS

| | | | |
|---|---|---|---|
| 3,507,931 | 4/1970 | Morris et al. | 260/683.65 |
| 3,542,671 | 11/1970 | Pollitzer | 260/683.68 |
| 3,632,835 | 1/1972 | Mitsche et al. | 260/683.68 |
| 3,691,255 | 9/1972 | Sinji Takase et al. | 260/683.68 |
| 3,836,597 | 9/1974 | Sie | 260/683.65 |

*Primary Examiner*—Delbert E. Gantz
*Assistant Examiner*—G. J. Crasanakis

[57] ABSTRACT

Process for isomerizing saturated hydrocarbons in the presence of a catalyst composition comprised of platinum or palladium on a fluorine-containing mordenite-type aluminosilicate, the fluorine having been introduced to the composition by halogenation with a fluorine-containing hydrocarbon halide.

15 Claims, No Drawings

ISOMERIZATION OF SATURATED HYDROCARBONS WITH MORDENITE CATALYST CONTAINING FLUORINE AND CHLORINE

This is a continuation of application Ser. No. 207,523, filed Dec. 13, 1971 and now abandoned.

BACKGROUND OF THE INVENTION

1. Field of the invention

This invention relates to a process for isomerizing saturated hydrocarbons. More particularly, it relates to a process for isomerizing a saturated hydrocarbon or a saturated hydrocarbon mixture to convert the same to a more highly branched saturated hydrocarbon or hydrocarbon mixture.

The present invention is also concerned with isomerizing alicylic hydrocarbons contained in petroleum hydrocarbons to convert the same to other isomers.

Furthermore, it is also concerned with ring-opening alicyclic hydrocarbons contained in petroleum hydrocarbons to convert the same to aliphatic hydrocarbons. As a manner in which the invention is utilized it is also concerned with conversion of aromatic hydrocarbons contained in petroleum hydrocarbons by saturation of the aromatic rings with hydrogen to alicyclic hydrocarbons as well as to isomerization or ring-opening to aliphatic saturated compounds of the resulting alicyclic compounds.

2. Description of the prior art

Various properties are required for gasoline fuel, including distillation characteristics, being free from corrosiveness, and appropriate volatility. Among them, high octane value is regarded to be critical.

Aromatic hydrocarbons, olefin hydrocarbons and highly branched saturated hydrocarbons are known to posses high octane values. The highly branched hydrocarbons are superior to the other hydrocarbons in that there is with the former less difference between the octane value according to the research method and that according to the motor method, that is, due to the lower sensitivity of the hydrocarbons.

The gasoline is a mixture of a variety of hydrocarbon compounds. The highly volatile of these, with boiling points below 85°C., are ordinarily olefin and saturated hydrocarbons having low molecular weights for the most part but most are saturated hydrocarbons.

For use in the highly developed gasoline engine is needed a gasoline containing in the low-boiling component low molecular weight saturated hydrocarbons possessing high octane values such as, for example, isopentanes and isohexanes, because gasoline is required to have high octane values throughout all the distillates.

In petroleum refining industry there have been divised and put into practical use various processes for isomerizing saturated hydrocarbon compounds to produce highly branched hydrocarbon compounds.

All of these isomerization processes are catalytic isomerization processes effected by the use of a catalyst. The catalysts used in these processes may be broadly classified into three classes: Metal halide catalysts of Friedel-Crafts type such as aluminium chloride or bromide used in combination with anhydrous hydrogen chloride or bromide; so-called dual functional catalysts comprising a metal component of hydrogenating function such as nickel, platinum or palladium carried on a refractory oxide such as alumina or silica-alumina; and platinum-alumina-halogenide composite catalysts.

Using a catalyst mainly composed of a metal halide such as aluminium chloride in the isomerization reaction of hydrocarbons containing more carbon atoms than pentane side reactions occur such as polymerization, condensation, disproportionation and cyclization with rapid deterioration of the catalyst. Moreover, the catalyst, which is highly corrosive, requires the use of a corrosion-resistant alloy for the main parts of the equipment. In addition, it is disadvantageous that the aluminium chloride sludge withdrawn from the equipment should be made harmless by means of, for example, neutralization or combustion.

On the other hand, so-called dual functional catalysts such as platinum-alumina, which are free from the afore mentioned disadvantages of aluminium-chloride catalyst, require use of a relatively high temperature in carrying out the reaction in order to attain a practically high reaction rate.

As well known, the lower the temperature the more favorable is the composition of paraffin hydrocarbon isomers at thermodynamic equilibrium to the highly branched isomer. Consequently, octane value of the product in the process using a dual functional catalyst, which requires a high reaction temperature, is controlled by the thermodynamic equilibrium in the same way as is the composition of isomers in the product.

Although composite catalysts of platinum-alumina with impregnated aliminium chloride thereupon by such a means as sublimation or impregnation, which are considered to be catalysts with combined merits of aluminium-chloride catalyst being active at low temperatures and of binarily functional catalyst being free from corrosiveness, requiring no activator such as hydrogen chloride and generating no harmful sludge, have been found to be effective at relatively low temperatures with little side reactions and are superior to the former two, they are disadvantageous in that the catalyst will be poisoned unless water content of the starting hydrocarbon is maintained below a few p.p.m. as well as regeneration of the deteriorated catalyst cannot be easily made.

Recently, crystalline aluminosilicate of zeolite type have drawn attention as a carrier being superior to alumina or silica-alumina. Catalysts composed of combination of platinum and crystalline aluminosilicate of zeolite type have been found to exert high catalytic activities. According to the descriptions by J. A. Labo, P. E. Pickart and R. L. Maize, catalyst MB 5390 manufactured by Department of Molecular Sieve Products of Linde Corporation, Tonawanda, N.Y., U.S.A., a division of Union Carbide Corporation, is water-proof and effectively used in the isomerization reaction of n-pentane and n-hexane at a reaction temperature from 335° to 340°C. [Industrial and Engineering Chemistry Vol. 53, No. 9, P. 735 (1961)]. The catalyst has been demonstrated on the basis of X-ray diffraction pattern and chemical analysis to be Molecular Sieve Y decationized and carrying a small amount of palladium [Noboru Yamamoto, Kataundo Fujii and Yoshitaka Damaru, Journal of Petroleum Society of Japan, vol. 9, No. 7, p. 531 (1966)].

In order to obtain hydrocarbons of high octane values, however, catalysts that are effective at lower temperatures are naturally desired.

Another crystalline aluminosilicate of zeolite type which may be used as a catalyst is mordenite. Mordenite catalysts including metallic hydrogenation component such as platinum or palladium, are effective at somewhat lower temperatures (of. the comparative examples below) but, with respect to improvement in octane value, there is a need for catalysts that are effective at even lower temperatures.

In order to enhance activities of platinum-alimina, palladium-alumina and other dual functional catalysts in the isomerization reaction, various methods are known; (1) addition of aluminum chloride by sublimation or impregnation, (2) introduction of halogens by reacting the catalyst with halogenating agents such as $CCl_4$, $S_2Cl_2$, $SOCl_2$, $PCOl_1$, or the like. An experiment has disclosed that these catalysts are effective at a lower temperature, viz., at 165°C. All of these catalysts, however, are hygroscopic as highly as is aluminium chloride as mentioned earlier and, on contacting with moisture, are reduced in catalytic activity so much that recovery of the activity by conventional means such as drying and calcination will be impossible.

On the other hand, we have discovered a method of introducing onto crystalline aluminosilicate of zeolite type a halogen by the reaction with a halogenated hydrocarbon (West German Patent Publication No. 2,010,551), wherein only the application to crystalline aluminosilicate of faujasite type is disclosed but no embodiment on mordenite.

Both mordenite and faujasite are classified in mineralogy under aluminosilicate of zeolite type, but the two are different in properties such as a chemical composition, crystal structure and reactivity with halogenated hydrocarbon. In particular, mordenite containing far smaller portion of aluminium than that in faujasite is not subjected to halogenation so readily as the latter or, if halogentated, to a halogen content as high as the latter.

For example, according to an experiment on halogenation of a commercially available reforming catalyst composed of substantially 100% alumina carrying platinum with $CCl_4$ (the third World Petroleum Congress, Amsterdam, 1964, by A. G. Goble and P. A. Laurance), there has been easily obtained a catalyst containing 13.6% chlorine. As we have previously demonstrated, treatment of zeolite of faujasite type with $CCl_2F_2$ yields zeolite containing 0.12% fluorine and 0.16% chlorine.

As set forth above, halogenation of mordenite with very low content of aluminum as compared with zeolite of faujasite type is difficult to conduct and for the same reason the combination with a halogen in an amount sufficient to improve catalytic activity has been unexpected; molar ratio of silica to alumina ($SiO_2/Al_2O_3$) is from 2 to 5 with the latter and above 9 with former. Such a case of halogenation has not been known at least regarding mordenite.

SUMMARY OF THE INVENTION

After extensive invenstigations of methods for enhancing the activity of catalysts comprising mordenite, we have now found that mordenite carrying platinum or palladium can be reacted with a halogenated hydrocarbon in a distinctly different manner from that with zeolite of faujasite type to afford catalysts which are effective at lower temperatures than those with catalysts of mordenite simply carrying platinum or palladium. Moreover, it has been found that when the halogenation reaction is carried out in the presence of steam there occurs no destruction of the crystal structure of mordenite at all even at temperatures higher than 350°C. to give halogen-containing mordenite.

The mordenite halogenated by the method set forth above is an isomerization catalyst of superior properties to those of non-halogenated mordenite. For example, isomerization of saturated hydrocarbons, hydrogenation of aromatic hydrocarbons and isomerization of a ring-opening reaction of alicyclic hydrocarbons, when using the mordenite in combination with an active metal component of hydrogenation function such as platinum or palladium, are effectively promoted at temperatures from 60°C. to 100°C. lower than with non-halogenated mordenite containing the active metal component of the same sort in the same proportion.

The present invention, which has been achieved on the basis of the above-described discovery, provides catalyst activities which are not adversely affected in the presence of moisture usually contained in the starting hydrocarbons to be subjected to such a reaction as isomerization or hydrogenation and which exert efficient and stable catalytic activities at temperatures far lower than those with heretofore known zeolite-containing catalysts in methods of hydrocarbon conversions such as isomerization of saturated hydrocarbons, hydrogenation of aromatic hydrocarbons and isomerization and ring-opening of alicyclic hydrocarbons using said catalysts.

It is therefore an object of this invention to provide a process for isomerizing petroleum hydrocarbon compounds or a mixture thereof to produce a petroleum hydrocarbon distillate containing a large proportion of more highly branched saturated hydrocarbons.

Another object of this invention is to provide a process for producing hydrocarbon distillates containing a large proportion of more highly branched saturated hydrocarbons by the treatment of hydrocarbons from shale oil or carbonization of coal or hydrocarbon distillates from Fischer-Tropsch synthesis by reaction of hydrogen and carbon dioxide.

A further object of this invention is to provide a process for producing gasoline having superior antiknocking property.

A still further object is to provide a method of preparing isomerization catalysts comprising natural or synthetic mordenite which are effective at temperatures lower than with the prior art catalysts and an isomerization process carried out using the same.

DESCRIPTION OF THE INVENTION

In the process of this invention may be used either natural or synthetic mordenite. An example of the natural mordenite is mordenite produced in Shiraishi City, Miyagi Prefecture, Japan. Synthetic mordenite products include one marketed by Norton Corporation under the trade name Zeolon Na and one marketed by the same corporation under the same Zeolon H. The mordenites mentioned above are merely illustrative and it is not intended to limit thereby the scope of mordenite usable in this invention.

Natural mordenite often contains exchangeable cations such as sodium, potassium, calcium, magnesium, strontium or other metal cations. In most cases, the mordenite has a low capacity of adsorbing compounds with a molecular size larger than 5 A. This is due to the small pore size of mordenite.

It is known that mordenite with such small pore size can be transformed into larger pore size mordenite by washing with water, ion exchange with sodium or ammonium ion or acid treatment with hydrochloric, sulfuric or another acid. Synthetic mordenite can also be transformed from the small-pore to larger-pore size. The larger pore type is also synthesized and commercially available.

Crystalline aluminosilicate of mordenite type including mordenite is a crystalline mass in which $SiO_4$ tetrahedrons and $AlO_4$ tetrahedrons are bonded to form a three-dimensional network structure. The networks form cavities within which cations such as metal cations or ammonium ions corresponding to the negative charge of $AlO_4$ are located. In the case of zeolite catalysts comprising other zeolite, for example, zeolite of faujasite type such as Y- or X-type zeolite, it is known that the alkali metal is ion-exchanged with a multivalent metal ion such as calcium, magnesium, lanthanum, dysprosium, zinc or cadmium to give a highly active catalyst which is effective in cracking, hydrocracking or alkylation reaction. On the other hand, catalysts obtained from mordenite containing these metals are of too low activities to be effective. This may be ascribed to difference in crystal structure between zeolite of mordenite type and zeolite of faujasite such as the Y or X type. According to the present invention, metal ions within the cavities of mordenite are exchanged with hydrogen or ammonium ions to form mordenite of hydrogen-ion or ammonium-ions type before use.

During the ion-exchanging treatment with hydrogen ion the bond

in mordenite is hydrolyzed thereby a portion of the aluminium atoms being removed. As well known, such a treatment does not lead to destruction of the crystal structure of mordenite. The mordenite from which a portion of aluminium has been removed by such a treatment is sometimes called aluminium deficient mordenite, some of which has a silica-alumina molar ratio (molar ratio $SiO_2/Al_2O_3$) more than 100.

According to this invention mordenite having a silica-alumina molar ratio in the range from 9 to 50 may be employed and one in the range from 9 to 35 is preferable.

Mordenite is available in a variety of forms such as fine powder, pulverized particle or small granule. It is not intended to set particular limitation to the shape and form in use, but the description is given merely for the convenience sake. Mordenite may be used after compacting, tabletting or extruding. In carrying out the molding, mordenite may be molded either alone or in mixture with a binding agent such as bentonite, diatomaceous earth, kaoline, alumina, silica, silica-alumina or another refractory inorganic oxide. No substantial influence to the catalytic activities will be associated with the mixing. The binding agent is used preferably after removal of cations of metals such as alkali and alkali earth metals.

A mixture of mordenite with a hydrosol or hydrogel, for example of alumina, silica or silica-alumina may also be employed for the molding. The binding agent may be used in a ratio up to 9 parts of the agent per part of the mordenite catalyst.

Platinum or palladium to be contained in the catalyst according to this invention is carried thereon by such a means as impregnation, blending or ion exchange. It is known that zeolite, being highly capable of exchanging ions, can carry a desired metal ion in an easy and efficient manner by means of ion exchange.

In preparing mordenite carrying platinum or palladium it is preferred to employ the ion-exchange method, but this invention may be carried out by impregnation or kneading. The platinum or palladium may be added either before or after molding.

Platinum or palladium is supported on the mordenite in an amount from 0.01 to 2.00% by weight on the basis of the finished catalyst. When carried in an amount below 0.01% by weight activity and stability will not be satisfactory. Use of the noble metal in an amount more than 2.00% by weight will not be economical with no increased effect at a sacrifice of economy.

Fluorine-containing halogen compounds used in the method of this invention are halogenated hydrocarbons including, for example, $CF_4$, $CHF_3$, $CH_2F_2$, $CCl_3F$, $CCl_2F_2$, $CClF_3$, $CH_2ClF$, $CHCl_2F$, $CHClF_2$, $CClF_2$—$CClF_2$, $CF_3C_6H_5$, $CF_2ClC_6H_5$ and $C_6H_5F$.

The process of this invention is particularly characterized by the reaction between the halogen compound and mordenite which is beyond all precedents and, is different from the reaction between zeolite of faujasite type and a halogenating agent as set forth above. Whereas zeolite of faujasite type gives chlorinated zeolite containing from 0 to 20% chlorine by the reaction with $CCl_4$, zeolite of mordenite type is combined with several percent chlorine at best. On the other hand, introduction of fluorine is more easily made with the mordenite type than the faujasite type. For example, when reacted with a halogen compound containing both fluorine and chlorine such as $CHClF_2$, mordenite is selectively attacked by flourine but faujasite does not show such selectivity.

Halogenation reaction of mordenite with the halogenating agent as illustrated above takes place at low temperature, at room temperature or below but is efficiently effected at an elevated temperature below 600°C. From experience the halogenation is preferably carried out at a temperature in the range from 160° to 320°C. with a high efficiency.

The halogen compound as illustrated above may be employed for the reaction with or without dilution with a gas such as helium, argon, carbon dioxide, air, nitrogen or oxygen.

When reacted at a relatively high temperature above 300°C., the halogen is readily introduced. On the other hand, crystal structure of aluminosilicate might be destroyed. Especially marked destruction is noted in cases of molecular sieves A, X and Y. Mordenite loses crystal structure, though to a lesser degree. However, it has been experimentally found that, when conducted in the presence of steam, the halogenation reaction with the halogenating agent is effected with no loss in crystallinity.

Halogenation with a relatively less reactive fluorinated hydrocarbon as illustrated by $CF_4$ and $CHF_3$ or a halogenated hydrocarbon such as polytetrafluorethylene or polytrifluorochlorethylene has now become feasible with no substantial destruction of zeolite structure.

It is possible to carry out the reaction between the halogenating agent and mordenite either continuously or batchwise. The reaction may be effected at reduced, normal or elevated pressure.

According to this invention a catalyst containing from 0.01 to 15% by weight, preferably from 0.05 to 13.0% by weight of halogen is employed. At a content below 0.01% by weight the effect of halogenation is not significant, whereas at a content above 15% by weight not only side reactions are increased but also the halogenation is not economical. This invention is characterized by the use of the catalyst prepared as above in isomerization hydrocarbons. The isomerization reaction of saturated hydrocarbons using the catalyst according to the invention may be conducted either in batch or in continuous operations.

The catalyst may be employed in the form of granule, tablet, extrudate, or powder. It may be used in a fixed bed, or in suspension or in a moving or fluidized bed. In order to maintain activity of the catalyst for a long period of time it is essential to use the same in the presence of a hydrogen-containing gas. However, as the isomerization reaction is accompanied only by change in hydrocarbon skeltone there occurs no substantial consumption of hydrogen. On the other hand, when the starting material contains olefinic, aromatic or alicyclic hydrocarbons, reactions including hydrogenation of the olefine and aromatic ring and ring-opening of the naphthene ring concurrently occur to consume hydrogen. In addition, light hydrocarbons such as methane produced by side reactions are accumulated in the reaction vessel in some cases when it is necessary to supply a small amount of hydrogen.

The reaction temperature is in the range from 15° to 350°C., preferably from 100° to 300°C. The reaction pressure is in the range from ordinary pressure to 90 kg./cm.$^2$G, preferably from 5 to 50 kg./cm.$^2$G.

Hydrogen to hydrocarbon molar ratio at the initiation of the reaction or at the inlet of the continuous reaction vessel is required to be in the range from 0.1 to 20, preferably from 0.5 to 10.

When a continuous reaction vessel is employed, the rate of charging the starting material may be from 0.05 to 20, preferably from 0.5 to 4, in terms of weight hourly space velocity.

Hydrocarbon suitable as the starting material is a saturated hydrocarbon containing from four to seven carbon atoms such as, for example, butane, pentane, hexanes, cyclohexane, methylcyclopentane or the like or a mixture thereof. Another example of the hydrocarbon suitable as the starting material is a distillate of light naphtha fraction initially boiling around 10°C. and having an end point of distillation below 90°C. As the hydrocarbon used as the starting material may be used straight run naphtha, hydrocracked naphtha, cracked naphtha and the like following or without fractional distillation. Although these may be used without removal of impurities such as sulfur and nitrogen compounds, the starting material is purified prior to use by acid, alkali, hydrogenation or adsorption (for example, with silica gel) treatment.

DESCRIPTION OF PREFERRED EMBODIMENTS

The process of this invention will be more clearly understood by referring to the following examples:

EXAMPLE 1

To 1000 ml. of 1 M aqueous solution of $NH_4NO_3$ was added 100 g. of commercially available synthetic mordenite in Na form ($SiO_2/Al_2O_3$ molar ratio, 11.1). The mixture was heated under reflux for 4 hours, followed by filtration to separate the mordenite and the mother liquor.

The above procedure was repeated three times to give $NH_4$ mordenite containing the residual Na as low as 0.05% by weight in terms of $Na_2O$($SiO_2/Al_2O_3$ molar ratio, 11.0), which was referred to as catalyst R.

15 g. of catalyst R was treated with aqueous solution of tetraamminpalladium (II) chloride prepared by adding to $Na_2PdCl_4$ a large excess of aqueous ammonia to afford the catalyst carrying 0.3% by weight palladium. The resulting catalyst was washed with water, kneaded with 3.75 g. of bentonite treated by refluxing three times with 1 M aqueous solution of ammonium chloride thereby reducing the concentration of Na ion. The kneaded mass was extruded through a syringe. The extruded dough was dried in air and then at 120°C. for 2 hours and calcinated in air at 500°C. for 3 hours. The catalyst thus prepared was referred to as catalyst A.

3 g. of catalyst A was filled in a quartz reaction tube and reduced under hydrogen at 450°C. for 3 hours. Then, $CHClF_2$ was passed at a flow rate of 50 ml./min. through the reaction tube maintained at a temperature of 180°C. for 20 min. together with $N_2$ gas at a flow rate of 100 ml./min.

After completion of the reaction unreacted materials were removed by passing $N_2$ gas at a flow rate of 100 ml./min. After cooled under nitrogen, the resulting catalyst was stored in a moisture-proof vessel. Analysis indicated 2.38% by weight of fluorine and 0.11% by weight of chlorine contained. This was referred to as catalyst B.

Using catalysts A and B and, for comparison's sake, a commercially available zeolite catalyst of Pd-Y type (SK-200 catalyst manufactured by Linde Corporation, U.S.A.), as an example of zeolite of Y type, isomerization reaction of n-hexane was conducted in a stainless steel tubular reactor equipment. Conditions and results of the reactions are shown in Table 1. Distribution of the products was determined by gas chromatography when stationary state was confirmed 20 hours or longer after initiation of the reaction.

The results in Table 1 indicate that in order to attain a similar conversion zeolite catalyst of Pd-Y type required a reaction temperature at least 70°C. higher than that with Pd-mordenite catalyst A thus demonstrating superiority of the latter catalyst. It may be understood that halogenated mordenite catalyst B is far superior, because it afforded a similar conversion to that with non-halogenated catalyst A at a temperature at least 70°C. lower.

Table 1

| | Isomerization of n-hexane. | | | |
| | Starting material | Pd-Y | Catalyst A | Catalyst B |
| --- | --- | --- | --- | --- |
| Reaction conditions: | | | | |
| Temperature, °C. | | 350 | 280 | 210 |
| Pressure, kg./cm.$^2$G | | 30 | 30 | 30 |
| WHSV, g./g.hr. | | 2.3 | 2.3 | 2.3 |
| $H_2$/n—$C_6$ molar ratio | | 5 | 5 | 5 |
| Distribution of the products wt.%: | | | | |
| $C_1$ | | | 0.05 | 0.01 |

Table 1-continued

| | Isomerization of n-hexane. Starting material | Pd-Y | Catalyst A | Catalyst B |
|---|---|---|---|---|
| $C_2$ | | 0.01 | 0.25 | 0.02 |
| $C_3$ | | 0.11 | 2.55 | 0.23 |
| $iC_4$ | | 0.01 | 2.75 | 0.40 |
| $nC_4$ | | 0.02 | 0.77 | 0.08 |
| $iC_5$ | | 0.02 | 2.28 | 0.32 |
| $nC_5$ | | 0.03 | 0.72 | 0.09 |
| 2.2DMB | | 8.78 | 10.92 | 14.78 |
| 2.3DMB | | 4.25 | 6.92 | 7.58 |
| 2MP | | 36.92 | 32.85 | 34.50 |
| 3MP | | 23.38 | 19.68 | 20.36 |
| $n-C_6$ | 99.75 | 26.27 | 20.16 | 21.58 |
| MCP | 0.25 | 0.20 | 0.10 | 0.05 |
| Total: | 100.00 | 100.00 | 100.00 | 100.00 |
| Distribution of the $C_6$ isomers (mole%): | | | | |
| 2.2DMB | | 8.80 | 12.18 | 14.96 |
| 2.3DMB | | 4.26 | 7.65 | 7.67 |
| 2MP | | 37.10 | 36.29 | 34.92 |
| 3MP | | 23.53 | 21.66 | 20.61 |
| $n-C_6$ | | 26.32 | 22.22 | 21.84 |
| Total: | | 100.00 | 100.00 | 100.00 |

EXAMPLE 2

A quartz reaction tube was filled with 5 g. of catalyst A, through which was passed $CHClF_2$ at a flow rate of 50 ml./min. together with $N_2$ gas at a flow rate of 100 ml./min. at 200°C. for 10 min. After completion of the reaction volatile substances remaining in the catalyst was purged with $N_2$ gas for 1 hour and the resulting catalyst was cooled under $N_2$ gas and stored in a moisture-proof vessel, which was referred to as catalyst C.

Catalyst C contained 3.64% by weight of fluorine and 0.02% by weight of chlorine.

Using 2 g. of catalysts A and C respectively, hydrofined naphtha was treated in a similar equipment to one in Example 1 at a reaction pressure of 30 kg./cm.$^2$, a hydrogen to naphtha molar ratio of 5 and WHSV of 2.3 g./g.hr. The reaction temperatures were 200°C. with catalyst C and 200°C. and 280°C. with catalyst A.

Prior to charging the starting material reduction of the catalyst was made by passing dry hydrogen at a flow rate of 100 ml/min. (dried on molecular sieve 4A) at 390°C. for 3 hours.

In Table 2 are shown analytical results of the hydrofined naphtha used as the starting material and the reaction products. The values for the analysis of the products are those obtained 40 hours after initiation of the reaction. As understood from Table 2, not only on n-hexane as set forth in Example 1 but also on hydrogenatively purified naphtha, Catalyst C according to this invention has a far higher activity than that of Catalyst A in view of obvious differences in reaction temperature, content of isomers in the product oil as well changes in contents of benzene and naphthenes.

Table 2

| | | Isomerization of hydrogenatively purified | | | |
|---|---|---|---|---|---|
| | | Starting material | Catalyst A | Catalyst A | Catalyst C |
| Reaction conditions: | | | | | |
| Temperature, °C. | | | 200 | 280 | 200 |
| Pressure, kg./cm.$^2$G | | | 30 | 30 | 30 |
| WHSV, g./g.hr. | | | 2.3 | 2.3 | 2.3 |
| $H_2$/H.C molar ratio | | | 5 | 5 | 5 |
| Distribution of the products wt.%: | | | | | |
| $C_1$ | | 0 | 0 | 0.59 | 0 |
| $C_2$ | | 0 | 0 | 1.14 | 0 |
| $C_3$ | | 0 | 0 | 10.02 | 0.41 |
| $iC_4$ | | 0 | 0 | 5.64 | 1.33 |
| $nC_4$ | | 1.76 | 1.52 | 5.64 | 0.71 |
| $neoc_5$ | | 0.00 | — | 0.64 | 0.05 |
| $iC_5$ | | 16.15 | 14.22 | 24.70 | 29.07 |
| $nC_5$ | | 24.41 | 25.84 | 12.90 | 17.03 |
| 2.2DMB | | 0.42 | 0.84 | 6.26 | 7.78 |
| 2.3DMB | | 1.69 | 2.40 | 2.86 | 4.20 |
| 2MP | | 16.10 | 13.96 | 11.80 | 16.04 |
| 3MP | | 9.48 | 9.46 | 7.99 | 9.48 |
| $nC_6$ | | 20.48 | 20.86 | 7.33 | 8.68 |
| CP | | 1.88 | 1.97 | 0.94 | 1.61 |
| MCP | | 4.41 | 5.80 | 1.09 | 2.68 |
| CH | | 0.79 | 1.19 | 0.30 | 0.93 |
| Benzane | | 1.89 | 0.22 | 0 | 0.00 |
| Total: | | 100.00 | 100.00 | 100.00 | 100.00 |
| Distribution of the $C_5$ isomer composition mole%: | | | | | |
| $neoC_5$ | | | 0.00 | 1.66 | 0.33 |
| $i-C_5$ | | 39.82 | 35.50 | 64.60 | 62.85 |
| $n-C_5$ | | 60.18 | 64.50 | 33.74 | 36.82 |

Table 2-continued

| Isomerization of hydrogenatively purified | | | |
|---|---|---|---|
| | Starting material | Catalyst A | Catalyst A | Catalyst C |
| Total: | 100.00 | 100.00 | 100.00 | 100.00 |

| | Starting material | Catalyst A | Catalyst A | Catalyst C |
|---|---|---|---|---|
| Distribution of $C_6$ isomer composition mole %: | | | | |
| 2.2DMB | 0.88 | 1.78 | 17.27 | 16.84 |
| 2.3DMB | 3.51 | 5.05 | 7.90 | 9.10 |
| 2MP | 33.42 | 29.38 | 32.55 | 34.74 |
| 3MP | 19.68 | 19.90 | 22.05 | 20.53 |
| n—$C_6$ | 42.51 | 43.90 | 20.23 | 18.79 |
| Total: | 100.00 | 100.00 | 100.00 | 100.00 |

EXAMPLE 3

Isomerization reactions of n-butane were carried out respectively using catalysts A and C used in Example 2. A stainless steel tubular reactor was filled with 2 g. of catalyst and the reaction was conducted at a pressure of 15 kg./cm.$^2$, a hydrogen to butane molar ratio of 7 and a WHSV of 6 g./g.hr., the temperature being determined in such a way that a similar conversion was afforded.

Analytical values of the products are those obtained after 10 hours of the run.

As shown in Table 3, it may be understood that catalyst C is effective is isomerization of butane at a temperature far lower than that with catalyst A.

Table 3

| Isomerization of n-butane. | | | |
|---|---|---|---|
| | Starting material | Catalyst A | Catalyst B |
| Reaction conditions: | | | |
| Temperature, °C. | | 320 | 260 |
| Pressure, kg./cm.$^2$G | | 15 | 15 |
| WHSV g./g.hr. | | 6 | 6 |
| $H_2$/n—$C_4$ molar ratio | | 1 | 1 |

| | Starting material | Catalyst A | Catalyst B |
|---|---|---|---|
| Distribution of the products wt.%: | | | |
| $C_1$ | 0 | 0.25 | 0.19 |
| $C_2$ | 0 | 0.63 | 0.44 |
| $C_3$ | 0 | 2.17 | 1.50 |
| $iC_4$ | 0.30 | 42.64 | 46.41 |
| $nC_4$ | 99.70 | 54.31 | 51.46 |
| Total: | 100.00 | 100.00 | 100.00 |
| Distribution of the $C_4$ isomer composition mole %: | | | |
| i—$C_4$ | 0.30 | 43.93 | 49.32 |
| n—$C_4$ | 99.70 | 56.07 | 52.68 |
| Total: | 100.00 | 100.00 | 100.00 |
| Ratio of decomposition wt.%: | | | |
| $\Sigma C_1$—$C_3/\Sigma C_1$—$C_4$ | | 3.05 | 2.13 |

EXAMPLE 4

15 g. of catalyst R as prepared in Example 1 (NH$_4$ mordenite) was treated with an aqueous solution containing [Pt(NH$_3$)$_4$]$^{++}$ prepared by adding to K$_2$PtCl$_4$ a large excess of aqueous ammonia to give the catalyst carrying platinum as much as 0.3% by weight in terms of the metal.

After washed with water the mordenite was mixed with Na$^+$ free silica hydrogel at such a ratio that the former is contained as much as 75% by weight and the mixture was kneaded and extruded. The extruded dough was dried in air and then at 120°C. for 2 hours and calcinated at 500°C. for 3 hours. The resulting catalyst was referred to as catalyst D.

A quartz reaction tube was filled with Catalyst D and heated to 350°C. A gaseous mixture of F$_2$ClC—CClF$_2$ at 10 ml./min. and air at 400 ml./min. was passed through the reaction tube for 30 min., the gaseous mixture containing steam at a partial pressure of 15 mm.Hg by in advance passing through a scrubbing bottle filled with water. Dry air was then passed at a flow rate of 200 ml./min. at 350°C. for 1 hour to purge volatile substances on the catalyst. The resulting catalyst, which was cooled and stored in a moisture-proof vessel, was referred to as Catalyst E.

Catalyst E contained 1.02% by weight fluorine but no chlorine.

Catalysts D and E each weighing 2 g. were respectively filled in a stainless steel reaction vessel, in which isomerization of n-pentane was conducted at a reaction pressure of 20 kg./cm.$^2$G, a hydrogen to hydrocarbon molar ratio of 5 and a WHSV of 2.2 g./g.hr., the reaction temperature being 280°C. with Catalyst D and 220°C. with Catalyst E. Results of analysis of the products are shown in Table 4. The analytical values are those obtained 30 hours after initiation of supply of the starting material. As seen from Table 4, in cases of Catalyst D and E where palladium was replaced by platinum, too, Catalyst E treated according to the method of this invention is effective at a far lower temperature.

Table 4

| Isomerization of n-pentane. | | | |
|---|---|---|---|
| | Starting material | Catalyst D | Catalyst E |
| Reaction conditions: | | | |
| Temperature, °C. | | 280 | 220 |
| Pressure, kg./cm.$^2$G | | 20 | 20 |
| WHSV, g./g.hr. | | 2.2 | 2.2 |
| $H_2$/n—$C_5$ molar ratio | | 5 | 5 |
| Distribution of the products wt.%: | | | |
| $C_1$ | 0 | 0.19 | |
| $C_2$ | 0 | 0.42 | 0.06 |
| $C_3$ | 0 | 1.43 | 0.13 |
| $iC_4$ | 0 | 1.00 | 0.27 |

Table 4-continued

| Isomerization of n-pentane. | Starting material | Catalyst D | Catalyst E |
|---|---|---|---|
| $nC_4$ | 0 | 1.19 | 0.14 |
| $neoC_5$ | 0 | 0.14 | |
| $iC_5$ | 0.45 | 54.11 | 56.81 |
| $nC_5$ | 99.55 | 41.52 | 42.59 |
| Total: | 100.00 | 100.00 | 100.00 |
| Distribution of the $C_5$ isomer composition mole %: | | | |
| $neoC_5$ | | 0.15 | 0 |
| $iC_5$ | 0.45 | 56.50 | 57.16 |
| $nC_5$ | 99.55 | 43.35 | 42.84 |
| Total: | 100.00 | 100.00 | 100.00 |

EXAMPLE 5

Experiment 1

100 g. of natural mordenite having an $SiO_2/Al_2O_3$ molar ratio of 9.2, produced in Miyagi Prefecture, Japan, in an aqueous solution of 2N HCl was heated under reflux for 4 hours. The procedure was repeated nine times to give a mordenite in H form having an $SiO_2/Al_2O_3$ molar ratio of 20.5, which was referred to as Catalyst S.

Catalyst S, 15 g., was transferred into an aqueous solution containing $[Pt(NH_3)_4]^{++}$ ion prepared by adding to $K_2PtCl_4$ a large excess of aqueous ammonia. There was carried 0.3% by weight platinum. After washed with water, the mordenite was kneaded with bayerite hydrogel in an amount corresponding to 15% by weight in terms of $Al_2O_3$ on the basis of the mordenite, and the kneaded mass was molded. The extruded catalyst dough was dried in air and then at 120°C. for about 2 hours and calcinated in air at 500°C. for 3 hours. The catalyst thus obtained was referred to as catalyst F.

A stainless steel tubular high-pressure reactor was filled with 2 g. of catalyst F, with which isomerization of n-hexane containing moisture at 20 p.p.m. was conducted at a reation temperature of 280°C., a reaction pressure of 30 kg./cm.²G, a hydrogen to hydrocarbon molar ratio of 10 mol./mol. and a WHSV of 1.3 g./g.hr. In Table 5 are shown of results of composition analysis of the products obtained 250 hours after initiation of supply of the starting material.

Experiment 2

A quartz reaction tube was filled with 3 g. of catalyst F, which was dried and reduced under hydrogen at 450°C. for 3 hours. After cooled $CCl_2F_2$ at a flow rate of 50 ml./min. together with $N_2$ gas at a flow rate of 100 ml./min. was passed therethrough at 220°C. for 10 min. After completion of the reaction the resulting catalyst was cooled under $N_2$ gas for 1 hour to room temperature and stored in a moisture-proof vessel. The catalyst thus obtained was referred to as catalyst G, which contained 2.80% by weight fluorine and 0.2% by weight chlorine. The same high-pressure reaction vessel as in Experiment 1 was filled with 2 g. of catalyst G, with which isomerization of n-hexane containing moisture at 20 p.p.m. was conducted under the same reaction conditions as in Experiment 1 except that the reaction temperature was 220°C. Results of analysis of the products 250 hours after initiation of supply of the starting material are shown in Table 5. As seen from Table 5, as compared with catalyst F obtained by treating natural mordenite with hydrochloric acid and having platinum carried thereon, catalyst G obtained by halogenating catalyst F exerts a superior activity. It will also be understood that the starting material containing moisture may be treated for catalyst G.

Table 5

| Isomerization of n-hexane. | Starting material | Catalyst F | Catalyst G |
|---|---|---|---|
| Reaction conditions: | | | |
| Temperature, °C. | | 280 | 220 |
| Pressure, kg./cm.²G | | 25 | 25 |
| WHSV, g./g.hr. | | 1.3 | 1.3 |
| $H_2/n-C_6$ molar ratio | | 10 | 10 |
| Distribution of the products wt.%: | | | |
| $C_1$ | | | |
| $C_2$ | | 0.27 | 0.09 |
| $C_3$ | | 2.33 | 0.61 |
| $iC_4$ | | 0.73 | 0.39 |
| $nC_4$ | | 0.54 | 0.19 |
| $iC_5$ | | 0.77 | 0.22 |
| $nC_5$ | | 0.34 | 0.10 |
| 2.2DMB | | 8.93 | 13.03 |
| 2.3DMB | | 7.22 | 7.75 |
| 2MP | | 35.82 | 35.88 |
| 3MP | | 21.58 | 21.10 |
| $n-C_6$ | 99.75 | 21.47 | 20.52 |
| MCP | 0.25 | 0.14 | 0.12 |
| Total: | 100.00 | 100.00 | 100.00 |

| | Starting material | Catalyst F | Catalyst G |
|---|---|---|---|
| Distribution of $C_6$ isomer composition mole %: | | | |
| 22DMB | | 9.40 | 13.24 |
| 23DMB | | 7.60 | 7.88 |
| 2MP | | 37.69 | 36.50 |
| 3MP | | 22.71 | 21.48 |
| $n-C_6$ | | 22.59 | 20.89 |
| Total: | | 100.00 | 100.00 |

EXAMPLE 6

On 15 g. of catalyst S in Example 5 was carried 0.3% by weight palladium by adding the same to an aqueous solution containing $[Pd(NH_3)_4]^{++}$ ion prepared by adding to $Na_2PdCl_4$ a large excess of aqueous ammonia.

After washed with water the mordenite was added to an aluminum hydrosol in such as manner that the mordenite to $Al_2O_3$ weight ratio was 1. The alumina sol was then gelled. The mass was dried at 120°C. for 24 hours and calcinated in air at 500°C. for 3 hours. The resulting catalyst was referred to as catalyst H.

In a 2-liter quartz flask was placed 3 g. of catalyst H and, after heated at 300°C. under a reduced pressure of 20 mm.Hg., argon gas was introduced to a reduced pressure of 400 mm.Hg into the flask, which was then heated to 350°C.

A gaseous mixture of steam at a partial pressure of 15 mm.Hg and $CHF_3$ at a partial pressure of 125 mm.Hg, the total pressure being 150 mm.Hg, was mixed with $O_2$ gas at a partial pressure of 10 mm.Hg to a total pressure of 160 mm.Hg. In a 30-ml. gas burette was placed the resulting gaseous mixture under such conditions that total pressure was 150 mm.Hg and temperature was 50°C., which was then introduced into the flask containing catalyst H and argon gas. This procedure was repeated ten times at intervals of 15 min.

After heated under a reduced pressure of 20 mm.Hg at 250°C. for 3 hours the flask was filled with $N_2$ gas to ordinary pressure and cooled. The catalyst was discharged and stored, which was referred to as catalyst J. Analysis indicated that Catalyst J contained 0.86% by weight fluorine.

A stainless steel tubular reactor was filled with 2 g. each of the catalyst, through which $H_2$ gas was passed at a flow rate of 100 ml./min. at 280°C. Isomerization of n-pentane was conducted at a reaction temperature of 280°C. a reaction pressure of 15 kg./cm.$^2$G, a hydrogen to hydrocarbon molar ratio of 2 and a WHSV of 4.4 g./g.hr.

In Table 6 are shown results of composition analysis of the products obtained 80 hours after initiation of supply of the started material.

As seen from Table 6, as compared with catalyst H obtained by treating natural mordenite with hydrochloric acid and having palladium carried thereon, catalyst J obtained by halogenating catalyst H according to the method of this invention exerts a superior activity.

Table 6

| | Isomerization of n-pentane. | | |
|---|---|---|---|
| | Starting material | Catalyst H | Catalyst J |
| Reaction conditions: | | | |
| Temperature, °C. | | 280 | 280 |
| Pressure, kg./cm.$^2$G | | 15 | 15 |
| WHSV g./g.hr. | | 4.4 | 4.4 |
| $H_2$/n—$C_5$ molar ratio | | 2 | 2 |
| Distribution of the products wt.%: | | | |
| $C_1$ | 0 | | |
| $C_2$ | 0 | 0.06 | 0.14 |
| $C_3$ | 0 | 0.10 | 0.23 |
| $iC_4$ | 0 | 0.08 | 0.38 |
| $nC_4$ | 0 | 0 | 0.26 |
| $neoC_5$ | 0 | 0 | 0.07 |
| $iC_5$ | 0.45 | 57.07 | 59.70 |
| $nC_5$ | 99.55 | 42.69 | 39.22 |
| Total: | 100.00 | 100.00 | 100.00 |
| Distribution of the $C_5$ isomer composition mole%: | | | |
| $neoC_5$ | | 0 | 0.07 |
| $i—C_5$ | 0.45 | 57.21 | 60.35 |
| $n—C_5$ | 99.55 | 42.79 | 39.58 |
| Total: | 100.00 | 100.00 | 100.00 |
| Ratio of decomposition wt.%: | | | |
| $\Sigma C_1—C_4/\Sigma C_1—C_5$ | | 0.24 | 1.01 |

COMPARATIVE EXAMPLE

In aqueous solution of 2N-HCl was heated under reflux 100 g. of synthetic mordenite having an $SiO_2/Al_2O_3$ molar ratio of 11.1 for 4 hours. The procedure was repeated three times to give a mordenite in H form containing 0.04% by weight $Na_2O$ and having an $SiO_2/Al_2O_3$ molar ratio of 65. The catalyst was referred to as catalyst T. Into an aqueous solution containing $[Pd(NH_3)_4]^{++}$ ion prepared by adding to $Na_2PdCl_4$ a large excess of aqueous ammonia was transferred 15 g. of the catalyst, on which 0.3% by weight palladium was thereby carried. After washed with water, the resulting catalyst was kneaded with 3.75 g. of bentonite from which most portion of $Na^+$ ion had been in advance removed and the kneaded mass was molded. The molded mass was dried in air and then at 120°C. for 2 hours and calcinated in air at 500°C. for about 3 hours. The catalyst thus prepared was referred to as catalyst K.

A quartz reaction tube was filled with 3 g. of Catalyst K, which was then dried and reduced under hydrogen at 450°C. for 3 hours. After cooled, the reduced catalyst was contacted with $CHF_3$ at a flow rate of 10 ml./min. together with $N_2$ gas (in advance passed through water) at a flow rate of 200 ml./min. for 1 hour. After completion of the reaction the resulting catalyst was cooled under $N_2$ gas for about 1 hour to room temperature and then stored in a moisture-proof vessel. The catalyst thus prepared, which was referred to as catalyst L, contained 0.8% by weight fluorine.

A stainless steel tubular high-pressure reaction tube was filled with 2 g. of the catalyst K or L respectively, in which isomerization of n-hexane was conducted at a reaction temperature of 280°C., a reaction pressure of 20 kg./cm.$^2$G, a hydrogen-hydrocarbon molar ratio of 3 mol./mol. and a WHSV of 3.5 g./g.hr. In Table 7 are shown results after 47 hours of run. As seen from Table 7, the effect of halogenation cannot be produced with the mordenite extremely deficient in Al which has an $SiO_2/Al_2O_3$ molar ratio of 65 and there is almost no difference in activity between the non-halogenated catalyst K and the halogenated catalyst L. It is therefore critical that $SiO_2/Al_2O_3$ molar ratio of mordenite is smaller than 50.

Table 7

| | Isomerization of n-hexane. | | |
|---|---|---|---|
| | Starting material | Catalyst K | Catalyst L |
| Reaction conditions: | | | |
| Temperature, °C. | | 280 | 280 |
| Pressure, kg./cm.$^2$G | | 20 | 20 |
| WHSV, g./g.hr. | | 3.5 | 3.5 |
| $H_2$/n—$C_6$ molar ratio | | 3 | 3 |
| Distribution of the products wt.%: | | | |
| $C_1$ | | 1.32 | 1.36 |
| $C_2$ | | 14.37 | 11.98 |
| $C_3$ | | 1.76 | 2.97 |
| $iC_4$ | | 2.26 | 2.53 |
| $nC_4$ | | 3.73 | 2.80 |
| $iC_5$ | | 3.38 | 1.36 |
| $nC_5$ | | 9.10 | 9.77 |
| 22DMB | | 5.45 | 5.74 |
| 23DMB | | 25.81 | 26.58 |
| 2MP | | 16.98 | 17.41 |
| 3MP | 99.75 | 15.83 | 17.39 |
| n—$C_6$ | 0.25 | 0.11 | 0.12 |
| MCP | | | |
| Total: | 100.00 | 100.00 | 100.00 |

| | Starting material | Catalyst K | Catalyst L |
|---|---|---|---|
| Distribution of the $C_6$ isomer composition mole%: | | | |
| 22DMB | | 12.38 | 12.70 |
| 23DMB | | 7.46 | 7.46 |
| 2MP | | 35.24 | 34.52 |
| 3MP | | 23.24 | 22.74 |
| n—$C_6$ | | 21.68 | 22.58 |
| Total: | | 100.00 | 100.00 |

EXAMPLE 7

A quartz reaction tube was filled with 3 g. of Catalyst D obtained in Example 4 and, while heating the catalyst at 350°C., $N_2$ gas was passed therethrough at a flow rate of 50 ml./min.

After 3 hours, the flow rate of $N_2$ gas was raised to 100 ml./min. and the temperature reduced to 240°C. $CF_2Cl_2$ gas was then passed at a flow rate of 40 ml./min., together with $N_2$ gas at a flow rate of 100 ml./min., over catalyst D heated at 240°C. for 12 hours.

Then, supply of the $CF_2Cl_2$ gas was stopped, whereas supply of the $N_2$ gas was continued for 3 hours at a flow rate of 100 ml./min. Heating was then discontinued. After cooled, the resulting catalyst was stored in a moisture-proof vessel, which was referred to as catalyst M. Analysis indicated that catalyst M contained 10.20% by weight fluorine and 0.01% by weight chlorine.

A stainless steel reactor was filled with 2 g. of catalyst M which was heated to 350°C. while passing hydrogen gas at a flow rate of 100 ml./min. under ordinary pressure. After 6 hours, the pressure was raised to 50 kg./cm.$^2$G and the temperature to 210°C. Isomerization of n-pentane was conducted under the pressure and temperature conditions cited above and at a WHSV of 2.5 g./g.hr. and a hydrogen to pentane molar ratio of 3.0.

From the analytical values of the products shown in Table 8, which are those obtained 480 hours after initiation of the reation, it will be understood that Catalyst M containing 10.20% by weight fluorine at 210°C. possesses an efficient activity.

Table 8

| Isomerization of n-pentane. | | |
|---|---|---|
| Reaction conditions: | | |
| Temperature, °C. | — | 210 |
| Pressure, kg./cm.$^2$G | — | 50 |
| WHSV | — | 2.5 |
| $H_2$/n—$C_5$ molar ratio | — | 3.0 |
| Catalyst | — | 2 g |
| Distribution of the products wt.%: | | |
| $C_1$ | 0 | 0.30 |
| $C_2$ | 0 | 0.62 |
| $C_3$ | 0 | 2.88 |
| $iC_4$ | 0 | 1.15 |
| n—$C_4$ | 0 | 0.87 |
| i—$C_5$ | 0.45 | 54.61 |
| n—$C_5$ | 99.55 | 39.57 |
| Total: | 100.00 | 100.00 |
| Distribution of the $C_5$ isomer composition: | | |
| i—$C_5$ | 0.45 | 58.00 |
| n—$C_5$ | 99.55 | 42.00 |
| Total: | 100.00 | 100.00 |

We claim:

1. In a process for the branch isomerization of saturated hydrocarbons at an elevated temperature of up to about 350°C. in the presence of a catalyst,
   the improvement which comprises conducting said process with a catalyst prepared by
   contacting a composition consisting essentially of from 0.01 to 2 weight percent of platinum or palladium supported on a natural or synthetic mordenite which is in hydrogen or ammonium form having a $SiO_2/Al_2O_3$ molar ratio in said mordenite of from 9 to 50 with a fluorine-containing halogenated hydrocarbon
   at a temperature from 0° to 600°C., to provide in said catalyst at least about .86 weight percent fluorine and containing chlorine in an amount less than about 0.2 weight percent.

2. Process according to claim 1 wherein the $SiO_2/Al_2O_3$ molar ratio in said mordenite is from 9 to 35.

3. Process according to claim 1 wherein the fluorine-containing halogenated hydrocarbon is a member selected from the group consisting of $CF_4$, $CHF_3$, $CH_2F_2$, $CCl_3F$, $CCl_2F_2$, $CClF_3$, $CH_2ClF$, $CHCl_2F$, $CHClF_2$, $CClF_2$—$CClF_2$, $CF_3C_6H_5$, $CF_2ClC_6H_5$ and $C_6H_5F$.

4. Process according to claim 1 wherein the contacting of said composition with a fluorine-containing halogenated hydrocarbon is conducted at a temperature from 160°C. to 320°C.

5. Process according to claim 1 wherein the contacting of said composition with a fluorine-containing halogenated hydrocarbon is conducted at a temperature from 300° to 600°C. in the presence of steam.

6. Process according to claim 1 wherein the isomerization reaction is conducted in a fixed-bed reactor.

7. Process according to claim 1 wherein the isomerization reaction is conducted in a fluidized-bed reactor.

8. Process according to claim 1 wherein the isomerization reaction is conducted at a temperature from 100° to 300°C. and a pressure from ordinary to 90 kg./cm.$^2$G, preferably from 5 to 50 kg./cm.$^2$G.

9. Process according to claim 1 wherein the isomerization reaction is conducted in a continuous reaction in which the hydrogen to hydrocarbon molar ratio at the inlet is from 0.1 to 20, preferably from 0.5 to 10.

10. Process according to claim 9 wherein the hydrocarbon compound to be isomerized is charged at a weight hour space velocity from 0.05 to 20.

11. Process according to claim 1 wherein the hydrocarbon compound to be isomerized is a saturated hydrocarbon containing from four to seven carbon atoms or a light naphtha fraction composed of distillates in the range from 10° to 90°C.

12. The process of claim 1 wherein said catalyst includes up to 10 weight percent fluorine.

13. Process according to claim 1 wherein said composition also includes a member of the group selected from bentonite, diatomaceous earth, kaolin, alumina, silica and silica-alumina as a binding agent.

14. Process according to claim 1 wherein said composition is contacted with said fluorine-containing halogenated hydrocarbon diluted with a gas selected from the group consisting of helium, argon, carbon dioxide, air, nitrogen and oxygen.

15. Process according to claim 1 wherein the catalyst from 0.05 to 0.2% by weight of chlorine and .86 to 13.0% by weight of fluorine.

* * * * *

UNITED STATES PATENT OFFICE
CERTIFICATE OF CORRECTION

PATENT NO. : 3,932,554
DATED : January 13, 1976
INVENTOR(S) : Sinji Takase et al It is certified that error appears in the above-identified patent and that said Letters Patent are hereby corrected as shown below:

Col. 3, line 11 "PCOL," should read --$POCl_2$--

Col. 10 in Table 2, title should read

--Isomerization of hydrogenatively purified naphtha--

Signed and Sealed this eighth Day of June 1976

[SEAL]

Attest:

RUTH C. MASON
*Attesting Officer*

C. MARSHALL DANN
*Commissioner of Patents and Trademarks*